United States Patent [19] [11] 4,042,331
Schmidt et al. [45] Aug. 16, 1977

[54] PROCESS FOR THE DETERMINATION OF THE BORON CONTENTS OF PURE HALOGENSILANES

[75] Inventors: Dietrich Schmidt, Burghausen; Johann Hofer, Kirchdorf; Winfried Lang, Burghausen; Erich Bildl, Holzoster, all of Austria

[73] Assignee: Wacker-Chemitronic Gesellschaft fur Elektronik-Grundstoffe mbH, Burghausen, Germany

[21] Appl. No.: 737,307

[22] Filed: Nov. 1, 1976

[30] Foreign Application Priority Data

Dec. 23, 1975 Germany .............................. 2558183

[51] Int. Cl.² ............................................. G01N 31/12
[52] U.S. Cl. ............................. 23/230 PC; 23/253 PC
[58] Field of Search ...................... 23/230 PC, 253 PC

[56] References Cited
U.S. PATENT DOCUMENTS 3,403,003  9/1968  Morgenthaler ................ 23/230 R X
3,540,861  11/1970  Bradley et al. ................ 23/230 R X Primary Examiner—Robert M. Reese
Attorney, Agent, or Firm—Allison C. Collard

[57] ABSTRACT

Process for the determination of the boron content of pure halogensilanes especially silicon tetrachloride and trichlorosilane, which contain up to 0.1% of atoms of acceptors and donors, which comprises the steps of converting the halogen silanes into the gaseous state in a testing apparatus by contacting said halogensilanes with an evaporator surface heated to a temperature ranging from 80° C to 350° C, passing the generated gases to a support heated to the decomposition temperature of the gases whereby the released silicon is deposited on the support, removing the support and the deposit thereon from the testing apparatus and determining the boron content by calculation from the measured value of the specific resistance of the support plus the deposited silicon. It should be understood that all parts of the testing apparatus which come into contact with the generated gas, with the exception of the support heated to the required deposition temperature, should be at the temperature above 80° C, but below the decomposition temperature of the halogensilane.

8 Claims, 1 Drawing Figure

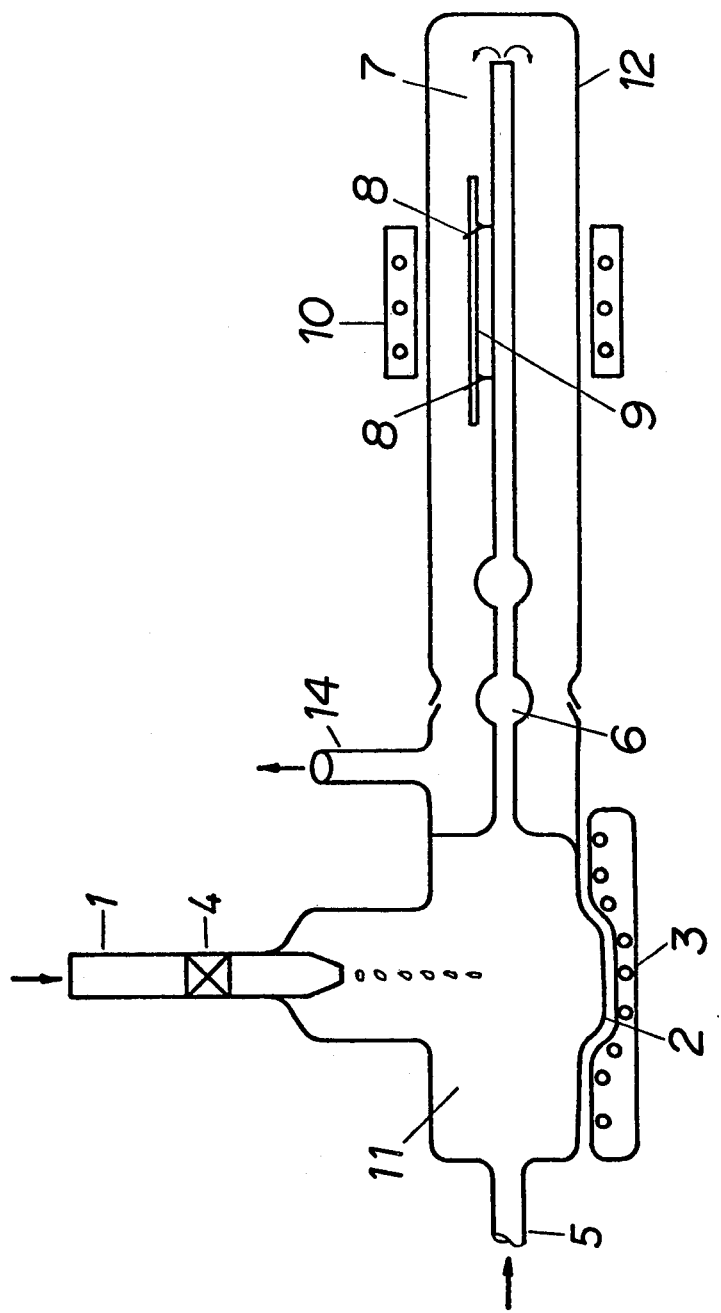

PROCESS FOR THE DETERMINATION OF THE BORON CONTENTS OF PURE HALOGENSILANES

The present invention relates to a process for determining the boron content of pure halogensilanes, especially silicontetrachloride and trichlorosilane, which contain acceptors and donors at a maximum of 0.1 atom%.

The preparation of silicon for semiconductor purposes, which is conventionally effected by decomposition of volatile halogen compounds, e.g. trichlorosilane requires starting materials of highest purity. The reason for this requirement is that impurities, such as especially boron, arsenic or phosphorus, will act as an undesirable doping agent on the silicon. The greatest difficulty in this respect is presented by boron, which due to its unfavorable distribution coefficient of about 0.8, and its low evaporation coefficient of about $10^{-5}$ cm/sec, can no longer be removed from the silicon by crucible-free zone melting. An accurate testing method for the determination of the acceptor and donor contents in the starting materials is therefore of highest significance.

A testing method is already known from DT-OS 15 23 001 for determining substances that will act as donors for silicon, as e.g. phosphorus and arsenic and their compounds. According to that process, a specimen of the halogensilane to be tested is decomposed in mixture with hydrogen on an inductively heated silicon support and the released silicon is deposited thereon. Subsequently, the silicon is separated from the support and its specific resistance is determined from which the donor content can be calculated. In order to prevent a compensatory doping by acceptor substances which would falsify the measuring result, halogenhydride is mixed with the halogensilane in addition to hydrogen, whereby the deposition of acceptor substances, e.g. boron, is substantially avoided at the chosen temperature.

It is the object of the present invention to provide an effective testing method for determining the amount of boron as well.

This is accomplished, according to the invention, by converting the halogensilanes into a gaseous state in a suitable testing apparatus by contacting them with an evaporator surface having a temperature between 80°C and 350°C provided in the testing apparatus. In this method, it is necessary that all the parts of the testing apparatus which come into contact with the generated gas - with the exception of the supports heated to the required deposition temperature - should reach a temperature above 80°C, which lies however below the decomposition temperature of the halogensilane; furthermore, that the gases are decomposed on a heated support, the released silicon deposited on the support and the obtained silicon body be freed, if necessary, by several zone drawing operations, from all impurities except boron, and the boron content then to be determined by means of a resistance meter.

In the following, the process of the invention will be more fully described in connection with the accompanying drawing in which a testing apparatus is illustrated by way of example in a schematic showing.

Referring now to the drawing, the test apparatus for determining the boron content of a specimen is shown to comprise a tube 1 through which the distilled pure halogensilane is made to drop onto an evaporator surface 2 which is heated by a heating device 3 to a temperature between 80°C and 350°C, preferably between 220°C and 280°C. The testing apparatus is preferably made of quartz. The specimens consist e.g. of disiliconhexachloride, dichlorosilane, and particularly of silicontetrachloride and trichlorosilane. The heating device 3 may be a resistance heater. The rate of admission of the specimen dropped onto the evaporator surface may be controlled by a metering valve 4.

In the preferred embodiment described, all parts of the apparatus which come into contact with the generated gas are maintained at a temperature above 180°C, but below the decomposition temperature of the halogensilane, the only exception being the support heated to the deposition temperature, as explained hereinbelow.

When the liquid halogensilane hits the evaporator surface 2, it will be quantitatively converted into the gaseous state, together with all impurities contained in traces therein. If higher boron complexes are present, they are split up in this operation and the component pieces are evaporated. It is advantageous to introduce repurified hydrogen through a tube 5; a saturated gas will then form with the halogensilane in a chamber 11. From the chamber, the gas is made to pass for better intermingling through a mixing device consisting of several ball-shaped spaces 6 and reaches thereafter the deposition chamber proper, indicated by numeral 7.

In chamber 7, the support 9 for the silicon to be deposited is mounted on two holding members 8; the support consists substantially of a monocrystalline thin silicon rod having a specific resistance of more than 5,000 ohm .cm, P. Instead of a thin silicon rod, other shapes may be used, for instance silicon discs.

According to a preferred mode of operation, the heating up of support 9 can be effected by an induction heating coil 10.

It is advantageous to heat only the portion of the silicon rod 9 which lies between holding members 8, up to the temperature for decomposition of the halogensilane, which is in the case of trichlorosilane, about 1,100° to 1,200°C, in order to prevent the holding members from being baked together with the depositing silicon. All other parts of the testing apparatus, which get into contact with the gas, must have a temperature over 80°C, according to the preferred mode of operation, over 180°C, but of course below the decomposition temperature of the halogensilane, in order to avoid deposition of the gas components of higher boiling point on the walls of the apparatus. In practice, this is accomplished by covering the evaporation chamber proper - 11 - for instance, with an asbestos ribbon so that the heating-up of the evaporator surface 2 by the coil 3 is sufficient to avoid a drop in temperature of the wall of the apparatus below the critical value of 80°C, or in the preferred embodiment, 180°C. The deposition chamber 7, on the other hand, should be kept relatively short, since due to heat dissipation of the inductively heated support 9, a drop of temperature below 80°C or 180°C respectively, will be avoided.

As a matter of principle, it would be feasable to place the entire testing apparatus into a furnace whose interior temperature lies above 80°C, or 180° C, respectively. The residual gases escape through a tube 14. After the entire specimen has evaporated and all the silicon released has been deposited on support 9, the latter is removed from the apparatus by pulling off the quartz cylinder 12 which confines the decomposition chamber.

Impurities are then removed from the support, preferably by zone drawing in about five to ten courses in vacuo.

During the purification process, impurities such as phosphorus, arsenic, aluminum, gallium, or indium are removed quantitatively from the silicon crystal, while the boron content remains practically unchanged.

Subsequently, the boron content is determined by measuring the specific resistance of the test rod in a conventional manner. In a preferred embodiment of the process, the deposit is not separated from the support, but the resistance contribution of the monocrystalline thin silicon rod substracted from the measured resistance value.

When the phosphorus content or the content of other impurities is low compared to the boron content, or when it is low and/or known, the deposited silicon body is converted into monocrystalline material mostly by only one zone drawing operation in a protective gas, e.g. argon. In this case, the rate of dropping of the halogensilane was high and thus the deposition of silicon rapid. When however the dropping rate was low and silicon deposition consequently slow, zone drawing under a protective gas is mostly dispensable, since slowly deposited silicon already shows monocrystalline areas whose specific resistance can easily be determined by a 4-point measurement.

The calculation of the boron content from the specific resistance is made in a known manner, for instance, with the use of the Tables of D.J. Irvin in "Bell System Technical Journal", vol. 41, page 387 abd. foll., 1962.

In the following, the process according to the invention will be more fully described in a specific example, with reference to the above described drawing, but it should be understood, that this is only given by way of illustration and not of limitation.

Example

In the apparatus described above, a support consisting of a thin monocrystalline silicon rod was mounted; the rod was about 7 cm long, 6.2 g in weight, and had a specific resistance of 5000 ohm. cm, P. The air was subsequently expelled by introduction of hydrogen. After the evaporation surface had been heated to 250°C and the support heated to 1,100°C by the induction heating coil, 300 g trichlorosilane were passed dropwise onto the evaporator surface and the gas generated thereby was propelled into the decomposition chamber proper, where the released silicon was deposited on the support. By insulation with asbestos, a drop in temperature of the wall of the apparatus below 200°C was effectively avoided. The evaporation of the trichlorosilane occurred within about 120 minutes without leaving any residue on the evaporator surface. After all the trichlorosilane had evaporated, the apparatus was rinsed for several minutes with hydrogen and the support was then removed with the deposited silicon, after cooling. Its weight was 14.4 g. Then, the support with the deposited silicon was purified by crucible-free zone drawing in vacuo in seven drawing operations and its specific resistance determined at 190 ohm. cm, P corresponding to a specific resistance of the deposited silicon of 110 ohm. cm, P. The boron content of the deposited silicon is calculated therefrom at $4.43 \cdot 10^{14}$ atoms, corresponding to an impurity of the tested trichlorosilane of effective boron in the deposition of about 0.3 ppb.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and intended to be, within the full range of equivalence of the following claims.

What is claimed is:

1. A process for the determination of the boron content of pure halogen-silanes which contain up to 0.1% of atoms of acceptors and donors, which comprises the steps of converting the halogen silanes into the gaseous state in a testing apparatus by contacting said halogensilanes with an evaporator surface heated to a temperature ranging from 80°C to 350°C, passing the generated gases to a silicon support heated to the decomposition temperature of the gases whereby the released silicon is deposited on the support, removing the support and the deposit thereon from the testing apparatus and determining the boron content by calculation from the measured value of the specific resistance of the support plus the deposited silicon, with the proviso that all parts of the testing apparatus which come into contact with the gas should be at a temperature above 80°C, but below the decomposition temperature of the halogensilane, with the exception of the support heated to the required deposition temperature.

2. The process claimed in claim 1, wherein the halogensilanes are silicontetrachloride or trichlorosilane.

3. The process claimed in claim 1, wherein the deposited silicon and its support are freed from impurities with the exception of boron by at least one step of zone-refining.

4. The process as claimed in claim 1, wherein the evaporator surface is heated to a temperature between 220° and 280° C.

5. The process according to claim 1, wherein the support consists of a substantially monocrystalline thin silicon rod having a specific resistance of 5,000 ohm . cm, P.

6. The process as claimed in claim 1, wherein the support is heated inductively.

7. The process as claimed in claim 1, wherein the support and the deposited silicon are not separated.

8. The process as claimed in claim 3, wherein the silicon body is freed from impurities with the exception of boron by 5 to 10 zone drawing operations before the specific resistance is determined.

* * * * *